(12) United States Patent
Heuft et al.

(10) Patent No.: US 7,872,155 B2
(45) Date of Patent: Jan. 18, 2011

(54) METHOD OF DEPROTECTION OF ALKYL ARYLAMINE ETHERS

(75) Inventors: Matthew A. Heuft, Oakville (CA); Jennifer A. Coggan, Cambridge (CA); Nan-Xing Hu, Oakville (CA)

(73) Assignee: Xerox Corporation, Norwalk, CT (US)

( * ) Notice: Subject to any disclaimer, the term of this patent is extended or adjusted under 35 U.S.C. 154(b) by 85 days.

(21) Appl. No.: 11/940,469

(22) Filed: Nov. 15, 2007

(65) Prior Publication Data
US 2009/0131721 A1    May 21, 2009

(51) Int. Cl.
*C07C 211/00* (2006.01)
(52) U.S. Cl. ...................................... 564/307
(58) Field of Classification Search ........................ None
See application file for complete search history.

(56) References Cited

U.S. PATENT DOCUMENTS

| | | | |
|---|---|---|---|
| 4,871,634 A | 10/1989 | Limburg et al. | |
| 5,230,976 A * | 7/1993 | Schank et al. | 430/58.2 |
| 5,368,967 A | 11/1994 | Schank et al. | |
| 5,702,854 A | 12/1997 | Schank et al. | |
| 5,709,974 A | 1/1998 | Yuh et al. | |
| 5,976,744 A | 11/1999 | Fuller et al. | |
| 7,138,555 B2 | 11/2006 | Goodbrand et al. | |
| 7,196,214 B2 | 3/2007 | Goodbrand et al. | |
| 7,227,034 B2 | 6/2007 | Bender et al. | |
| 7,238,456 B2 | 7/2007 | Bender et al. | |
| 2006/0111588 A1 | 5/2006 | Bender et al. | |
| 2006/0160002 A1 | 7/2006 | Qi et al. | |
| 2006/0222977 A1 | 10/2006 | Goodbrand et al. | |
| 2007/0087277 A1 | 4/2007 | Qi et al. | |
| 2007/0100164 A1 | 5/2007 | Coggan et al. | |

FOREIGN PATENT DOCUMENTS

JP          03294251       *   2/1990

OTHER PUBLICATIONS

JP03294251 STN Abstract, Kawasaki, N. 1 page.*
March, J. Advanced Organic Chemistry Reactions, Mechanisms, and Structure, 4$^{th}$ ed. 1992, 278-280. Previously provided by Applicant in an affadavit.*
Magano et al., 2-(*Diethylamino)ethanethiol, a New Reagent for the Odorless Deprotection of Aromatic Methyl Ethers*, J. Org. Chem., vol. 71, pp. 7103-7105 (2006).
U.S. Appl. No. 11/563,931, filed Nov. 28, 2006 to Bender et al.
U.S. Appl. No. 11/563,937, filed Nov. 28, 2006 to Bender et al.
U.S. Appl. No. 11/563,873, filed Nov. 28, 2006 to Bender et al.

* cited by examiner

*Primary Examiner*—Daniel M Sullivan
*Assistant Examiner*—Clinton Brooks
(74) *Attorney, Agent, or Firm*—Oliff & Berridge, PLC

(57) ABSTRACT

A method for deprotecting alkyl arylamine ethers to produce hydroxyl arylamine compounds by reacting the alkyl arylamine ether with a thiolate reagent. More specifically, a method for deprotecting alkyl arylamine ethers to produce hydroxyl arylamine compounds by reacting 2-(diethylamine) ethanethiolate with an alkyl arylamine ether to yield a hydroxy arylamine compound.

20 Claims, No Drawings

METHOD OF DEPROTECTION OF ALKYL ARYLAMINE ETHERS

TECHNICAL FIELD

This disclosure is generally directed to a method for producing hydroxy arylamine compounds, and particularly is directed to a method for deprotecting alkyl arylamine ethers to form hydroxy arylamine compounds.

RELATED APPLICATIONS

Commonly assigned, U.S. patent application Ser. No. 11/563,931 filed Nov. 28, 2006, describes a process for forming a triarylamine compound, comprising reacting an aniline and an arylchloride in the presence of a palladium ligated catalyst and a base.

Commonly assigned, U.S. patent application Ser. No. 11/563,873 filed Nov. 28, 2006, describes a process for forming a diarylamine compound, comprising reacting an aniline and an arylbromide in the presence of a palladium ligated catalyst and a base.

Commonly assigned, U.S. patent application Ser. No. 11/563,937 filed Nov. 28, 2006, describes an improved method for the preparation of derivatives of 4-aminobiphenyl using a ligated palladium catalyst in the presence of base.

Commonly assigned, U.S. patent application Ser. No. 11/263,671 filed Nov. 1, 2005, describes a process for the preparation of a tertiary arylamine compound, comprising reacting an arylhalide and an arylamine in an ionic liquid in the presence of a catalyst.

Commonly assigned, U.S. patent application Ser. No. 10/992,690 filed Nov. 22, 2004, describes a process for forming a tertiary arylamine compound, comprising reacting an arylbromide and an arylamine. For example, the application describes a process for forming N,N-diphenyl-4-aminobiphenyl, comprising reacting 4-bromobiphenyl and diphenylamine in the presence of a palladium-ligated catalyst.

Commonly assigned, U.S. Pat. No. 7,227,034 filed Nov. 22, 2004, describes a process for forming a 4-aminobiphenyl derivative arylamine compound, comprising: (i) providing a first disubstituted 4-aminobiphenyl compound; (ii) optionally formylating the first disubstituted 4-aminobiphenyl compound to form a bisformyl substituted compound, where the first disubstituted 4-aminobiphenyl compound is not a bisformyl substituted compound; (iii) acidifying the bisformyl substituted compound to convert formyl functional groups into acid functional groups to form an acidified compound; and (iv) hydrogenating the acidified compound to saturate at least one unsaturated double bonds in the acidified compound, wherein there is provided a second disubstituted 4-aminobiphenyl compound.

Commonly assigned, U.S. patent application Ser. No. 10/992,658 filed Nov. 22, 2004, describes a process for forming a 4-aminobiphenyl derivative arylamine compound, comprising: (i) providing an iodinated organic compound; (ii) substituting the iodinated organic compound at carboxylic acid groups thereof to provide ester protecting groups; (iii) conducting an Ullman condensation reaction to convert the product of step (ii) into an arylamine compound; and (iv) conducting a Suzuki coupling reaction to add an additional phenyl group to the arylamine compound in the 4-position relative to the nitrogen, to provide the 4-aminobiphenyl derivative arylamine compound.

Commonly assigned, U.S. patent application Ser. No. 11/094,683 filed Mar. 31, 2005, describes a process for forming an anhydrous alkali earth salt of a dicarboxylic acid of an arylamine compound, comprising reacting a dicarboxylic acid of an arylamine compound with an anhydrous alkali earth salt. The application also discloses a process for forming a siloxane-containing hole-transport molecule, comprising: reacting a dicarboxylic acid of an arylamine compound with an anhydrous alkali earth salt to form an anhydrous dicarboxylic acid salt of the arylamine compound; and reacting the anhydrous dicarboxylic acid salt of the arylamine compound with a siloxane-containing compound.

Commonly assigned, U.S. patent application Ser. No. 10/998,585 filed Nov. 30, 2004, describes a silicon-containing layer for electrophotographic photoreceptors comprising: one or more siloxane-containing compound; and one or more siloxane-containing antioxidant; wherein the siloxane-containing antioxidant is at least one member selected from the group consisting of hindered-phenol antioxidants, hindered-amine antioxidants, thioether antioxidants and phosphite antioxidants.

Commonly assigned, U.S. patent application Ser. No. 11/034,713 filed Jan. 14, 2005, describes an electrophotographic photoreceptor comprising a charge-generating layer, a charge-transport layer, and an overcoat layer comprised of a crosslinked siloxane composite composition comprising at least one siloxane-containing compound and metal oxide particles.

Commonly assigned, U.S. patent application Ser. No. 10/709,193 filed Apr. 20, 2004, describes a process for preparing an aryl iodide compound, comprising: reacting an aryl halide compound with a metal iodide, a metal catalyst and a catalyst coordinating ligand in at least one solvent to form an aryl iodide; and purifying the aryl iodide; wherein the solvent is heated to reflux during the reacting; wherein an aryl iodide yield of at least about 75% is obtained; and wherein the aryl iodide has a purity of at least 90%.

Commonly assigned, U.S. patent application Ser. No. 11/260,249 filed Oct. 28, 2005, describes a photoconductive member comprising: a charge generating layer; a charge transport layer; and a layer in contact with the charge transport layer comprising a substantially crosslinked resin of at least a phenol compound and a charge transport compound, wherein the charge transport compound is represented by A-(L-OR)$_n$ wherein A represents a charge transport component, L represents a linkage group, O represents oxygen, R represents a hydrocarbyl group, and n represents a number of repeating segments or groups.

The appropriate components and process aspects of each of the foregoing, such as the arylamine precursor materials and electrophotographic imaging members, may be selected for the present disclosure in embodiments thereof. The entire disclosures of the above-mentioned applications are totally incorporated herein by reference.

REFERENCES

Various overcoats employing alcohol soluble polyamides have been proposed. Disclosed in U.S. Pat. No. 5,368,967 is an electrophotographic imaging member comprising a substrate, a charge generating layer, a charge transport layer, and an overcoat layer comprising a small molecule hole transporting arylamine having at least two hydroxy functional groups, a hydroxy or multihydroxy triphenyl methane, and a polyamide film forming binder capable of forming hydrogen bonds with the hydroxy functional groups such as the hydroxy arylamine and hydroxy or multihydroxy triphenyl methane. This overcoat layer may be fabricated using an alcohol solvent. This electrophotographic imaging member may be used in an electrophotographic imaging process. Specific materials including ELVAMIDE® polyamide, N,N'-diphenyl-N,N'-bis (3-hydroxyphenyl)-(1,1'-biphenyl)-4,4'-diamine and bis-[2-methyl-4-(N-2-hydroxyethyl-N-ethyl-aminophenyl)]-phenylmethane are disclosed in this patent.

A crosslinked polyamide overcoat is known, comprising a crosslinked polyamide containing N,N'-diphenyl-N,N'-bis(3-hydroxyphenyl)-(1,1'-biphenyl)-4,4'-diamine, and referred to as LUCKAMIDE®. In order to achieve crosslinking, a polyamide polymer having N-methoxymethyl groups (LUCKAMIDE®) was employed along with a catalyst such as oxalic acid. This overcoat is described in U.S. Pat. No. 5,702,854, the entire disclosure thereof being incorporated herein by reference.

Disclosed in U.S. Pat. No. 5,976,744 is an electrophotographic imaging member including a supporting substrate coated with at least one photoconductive layer, and an overcoating layer. The overcoating layer includes hydroxy functionalized aromatic diamine and a hydroxy functionalized triarylamine dissolved or molecularly dispersed in a crosslinked acrylated polyamide matrix. The hydroxy functionalized triarylamine is a compound different from the polyhydroxy functionalized aromatic diamine.

Disclosed in U.S. Pat. No. 5,709,974 is an electrophotographic imaging member including a charge generating layer, a charge transport layer and an overcoating layer. The transport layer includes a charge transporting aromatic diamine molecule in a polystyrene matrix. The overcoating layer includes a hole transporting hydroxy arylamine compound having at least two hydroxy functional groups, and a polyamide film forming binder capable of forming hydrogen bonds with the hydroxy functional groups of the hydroxy arylamine compound.

Disclosed in U.S. Pat. No. 5,368,967 is an electrophotographic imaging member comprising a substrate, a charge generating layer, a charge transport layer, and an overcoat layer comprising a small molecule hole transporting arylamine having at least two hydroxy functional groups, a hydroxy or multihydroxy triphenyl methane, and a polyamide film forming binder capable of forming hydrogen bonds with the hydroxy functional groups such as the hydroxy arylamine and hydroxy or multihydroxy triphenyl methane. This overcoat layer may be fabricated using an alcohol solvent. This electrophotographic imaging member may be used in an electrophotographic imaging process. Specific materials including ELVAMIDE® polyamide and N,N'-diphenyl-N,N'-bis(3-hydroxyphenyl)-(1,1'-biphenyl)-4,4'-diamine and bis-[2-methyl-4-(N-2-hydroxyethyl-N-ethyl-aminophenyl)]-phenylmethane are disclosed in this patent.

Disclosed in U.S. Pat. No. 4,871,634 is an electrostatographic imaging member containing at least one electrophotoconductive layer. The imaging member comprises a photogenerating material and a hydroxy arylamine compound represented by a certain formula. The hydroxy arylamine compound can be used in an overcoat with the hydroxy arylamine compound bonded to a resin capable of hydrogen bonding such as a polyamide possessing alcohol solubility.

The disclosures of each of the foregoing patents and publications, and the disclosures of any patents and publications cited below, are hereby totally incorporated by reference. The appropriate components and process aspects of the each of the foregoing patents and publications may also be selected for the present compositions and processes in embodiments thereof.

BACKGROUND

Arylamine compounds can be used as hole transport materials for photoreceptor applications. In electrophotography, an electrophotographic imaging member may include the following active layers: (1) a charge generating layer containing a light-absorbing material, and (2) a charge transport layer containing charge transport molecules or materials. A hole transport material is a material that facilitates the transport of charge over the surface of the electrophotographic imaging member.

Many hole transport materials for photoreceptor applications contain hydroxy arylamine functionality. The term "arylamine" refers, for example, to moieties containing both aryl and amine groups. Exemplary aralkylene groups have the structure Ar—$NR_1R_2$, in which Ar represents an aryl group and $R_1$ and $R_2$ are groups that may be independently selected from hydrogen and substituted and unsubstituted alkyl, alkenyl, aryl, and other suitable functional groups. Production of a number of arylamine compounds, such as arylamine compounds that are useful as charge-transport compounds in electrophotographic imaging devices and processes, often involves synthesis of intermediate materials, some of which generally are costly and/or time-consuming to produce, and some of which involve a multi-step process.

For example, such hydroxy arylamine compounds are typically prepared via deprotection of an alkyl arylamine ether using trimethyl silyliodide or trimethyl silylchloride and sodium iodide in sulfolane. For example, a typical preparation of a hydroxy arylamine compound, N,N'-diphenyl-N,N'-bis(3-hydroxyphenyl)-[1,1'-biphenyl]-4,4'-diamine, from a methoxy arylamine compound, N,N'-diphenyl-N,N'-bis(3-methoxyphenyl)-[1,1'-biphenyl]-4,4'-diamine, is described below:

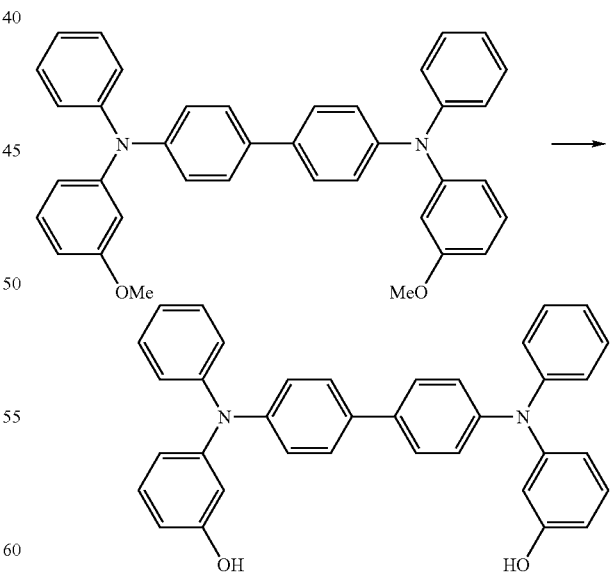

N,N'-diphenyl-N,N'-bis(3-hydroxyphenyl)-[1,1'-biphenyl]-4,4'-diamine is obtained by the demethylation of N,N'-diphenyl-N,N'-bis(3-methoxyphenyl)-[1,1'-biphenyl]-4,4'-diamine with trimethyl silylchloride and sodium iodide, in the presence of water, with sulfolane as the reaction solvent. The reaction is carried out at 60-65° C. for 6-7 hours under a nitrogen atmosphere. Aqueous sodium hydroxide scrubbers are used to neutralize methyl iodide, hydrogen iodide, and hydrochloric acid released during the reaction. Acidic volatile by-products are vacuum distilled prior to the precipitation of the crude N,N'-diphenyl-N,N'-bis(3-hydroxyphenyl)-[1,1'-biphenyl]-4,4'-diamine-sulfolane adduct by the addition of deionized water. The crude adduct is washed with aqueous sodium thiosulphate solutions and deionized water for iodide removal. The crude material undergoes three purification steps. The crude is dissolved in acetone by heating to 55° C. and reprecipitated by the addition of deionized water, for the removal of sulfolane and the formation of a N,N'-diphenyl-N,N'-bis(3-hydroxyphenyl)-[1,1'-biphenyl]-4,4'-diamine-water adduct. The N,N'-diphenyl-N,N'-bis(3-hydroxyphenyl)-[1,1'-biphenyl]-4,4'-diamine-water adduct is heated to 55° C. in acetone for dissolution and reprecipitated by the addition of heptane, for the removal of water and the formation of a N,N'-diphenyl-N,N'-bis(3-hydroxyphenyl)-[1,1'-biphenyl]-4,4'-diamine-acetone adduct. The N,N'-diphenyl-N,N'-bis(3-hydroxyphenyl)-[1,1'-biphenyl]-4,4'-diamine-acetone adduct is refluxed in heptane for azeotropic removal of acetone to give the purified N,N'-diphenyl-N,N'-bis(3-hydroxyphenyl)-[1,1'-biphenyl]-4,4'-diamine monomer.

This reaction is lengthy, can lead to higher costs, and can be very difficult to perform. The procedure requires a scrubber on the reaction to trap any methyl iodide, hydrogen iodide, and hydrochloric acid that is released during the reaction. The purification is complicated since the acidic volatile by-products must be removed by vacuum distillation prior to the precipitation or else side reactions can occur during the workup. An efficient process for the deprotection of arylamine compounds containing aromatic methyl ether groups is lacking in the industry.

Magano et al., *2-(Diethylamino)ethanethiol, a New Reagent for the Odorless Deprotection of Aromatic Methyl Ethers*, J. Org. Chem., vol. 71, 2006, pages 7103-7105, describes a new reagent for the deprotection of electron-deficient aromatic methyl ethers using 2-(diethylamine)ethanethiol. This compound is commercially available as a hydrochloric acid salt, is odorless during the purification, and leads to an easy purification procedure because an extraction can be performed to remove both the deprotecting reagent and the byproduct, 2-(diethylamino)ethyl methyl sulfide into the aqueous phase by quenching with dilute acid. However, according to Magano et al., these conditions are only suited to compounds which contain electron withdrawing groups on the aromatic ring. See Magano et al. at page 7105 ("The major limitation for this methodology has to do with the absence of electron-withdrawing groups on the ring.").

The reaction is performed by mixing the reagent, 2-(diethylamine)ethanethiol hydrochloric acid with sodium tert-butoxide in a solvent such as dimethylformamide, n-methyl-2-pyrrolidone, tetrahydrofuran, and dimethyl sulfoxide. The methoxy substituted substrate, is then added and the reaction heated at reflux until the reaction is complete. A workup and purification is then performed to give the desired hydroxy substituted compound.

SUMMARY

The above-disclosed methods of deprotection have particular deficiencies. First, the typical deprotection of an aromatic methyl ether using trimethyl silyliodide or trimethyl silylchloride and sodium iodide in sulfolane is difficult to perform, lengthy, and can be costly. The method of using 2-(diethylamine)ethanethiol disclosed by Magano et al. is reported to only be effective with electron-deficient aromatic methyl ethers. Thus, according to this information, the only option for deprotecting electron-donating alkyl arylamine ethers, is the typical, lengthy and costly method.

This disclosure addresses some or all of the above problems, and others, by providing an effective method for deprotecting alkyl arylamine ethers by reacting the protected compound with a thiol.

In an embodiment, this disclosure provides a method for deprotecting an alkyl arylamine ether to produce a hydroxyl arylamine compound, comprising: reacting a thiol reagent with an alkyl arylamine ether to yield a hydroxy arylamine compound.

In another embodiment, this disclosure provides a method for deprotecting an alkyl arylamine ether to produce a hydroxyl arylamine compound, comprising: reacting a 2-(diethylamine)ethanethiol with an alkyl arylamine ether to yield a hydroxy arylamine compound.

EMBODIMENTS

The present disclosure provides a method for deprotecting alkyl arylamine ethers by reacting the protected compound with a thiol. Generally, the reaction comprises reacting the protected alkyl arylamine ether with a thiol acid-salt reagent in the presence of a base and a solvent.

For example, the method of deprotecting the alkyl arylamine ether, N,N'-diphenyl-N,N'-bis(3-methoxyphenyl)-[1,1'-biphenyl]-4,4'-diamine, to produce the hydroxyl arylamine, N,N'-diphenyl-N,N'-bis(3-hydroxyphenyl)-[1,1'-biphenyl]-4,4'-diamine, is outlined by the following chemical equation:

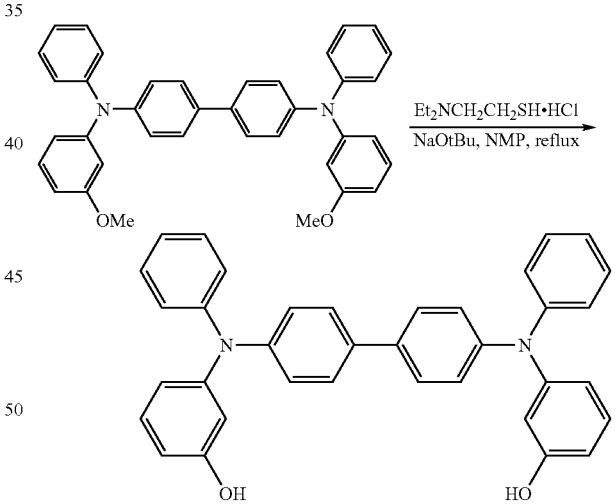

The reaction is performed by mixing the reagent, 2-(diethylamine)ethanethiol hydrochloric acid with sodium tert-butoxide in a solvent such as dimethylformamide, n-methyl-2-pyrrolidone, or tetrahydrofuran. The N,N'-diphenyl-N,N'-bis(3-methoxyphenyl)-[1,1'-biphenyl]-4,4'-diamine is added, and the reaction is heated at reflux until the reaction is complete. A workup and purification is then performed to give the desired hydroxy substituted compound.

According to the disclosure, the method can be used for deprotecting any desired arylamine ether, and particularly alkyl arylamine ethers. In an embodiment, the alkyl arylamine ether has the following formula:

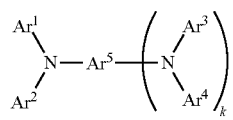

wherein $Ar^1$, $Ar^2$, $Ar^3$, $Ar^4$ and $Ar^5$ each independently represents a substituted or unsubstituted aryl group, or $Ar^5$ independently represents a substituted or unsubstituted arylene group, and k represents 0 or 1, wherein at least one of $Ar^1$, $Ar^2$, $Ar^3$ and $Ar^4$ comprises an alkyl arylamine ether to be deprotected. Where $Ar^1$, $Ar^2$, $Ar^3$, $Ar^4$, and/or $Ar^5$ are substituted by one or more groups, the substitutions can be selected from any suitable group such as silyl groups, nitro groups, cyano groups, halide atoms, amine groups, hydroxy groups, alkoxy groups, aryloxy groups, alkylthio groups, arylthio groups, aldehyde groups, ketone groups, ester groups, amide groups, carboxylic acid groups, sulfonic acid groups, and the like. In embodiments, the substituted or unsubstituted aryl groups can have, for example, from 1 to about 25 carbon atoms, such as from 1 to about 15 carbon atoms or from 1 to about 8 carbon atoms. In embodiments, the optional substituent groups can be, but are not limited to, alkoxy groups having from 1 to about 20 carbon atoms such as from 1 to about 10 carbon atoms; aryloxy groups having from about 6 to about 20 carbon atoms such as from about 6 to about 10 carbon atoms; alkylthio groups having from 1 to about 20 carbon atoms such as from 1 to about 10 carbon atoms; and arylthio groups having from about 6 to about 20 carbon atoms such as from about 6 to about 10 carbon atoms.

In embodiments, at least one of $Ar^1$, $Ar^2$, $Ar^3$, and $Ar^4$ comprises an alkyl arylamine ether to be deprotected. However, in other embodiments, two, three, or four of the $Ar^1$, $Ar^2$, $Ar^3$, and $Ar^4$ can comprise an alkyl arylamine ether to be deprotected.

In embodiments, the substituting ether may be an alkyl group having from 1 to about 20 carbon atoms, such as having from 1 to about 6 carbon atoms.

Although any suitable group can be present as the $Ar^5$ group, particular embodiments include those alkyl arylamine ethers where the $Ar^5$ group is a substituted or unsubstituted phenylene group, represented by formula (Ar5-1); a substituted or unsubstituted divalent condensed-ring polycyclic hydrocarbon group, represented by formulae (Ar5-2), (Ar5-3), (Ar5-4), and (Ar5-5), wherein $R_1$, $R_2$, $R_3$ and $R_4$ each independently represents a hydrogen atom, an alkyl group having 1 to 4 carbon atoms, an alkoxy group having 1 to 4 carbon atoms, a substituted or unsubstituted phenyl group, a substituted or unsubstituted aralkyl group or a halogen atom:

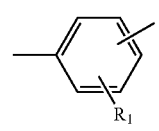
(Ar5-1)

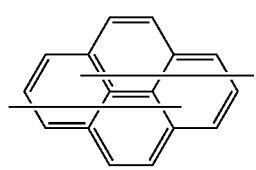
(Ar5-2)

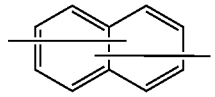
(Ar5-3)

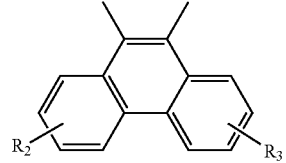
(Ar5-4)

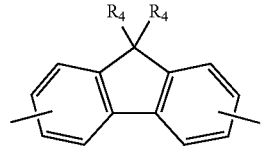
(Ar5-5)

The $Ar^5$ group may also be substituted or unsubstituted divalent condensed-ring heterocyclic group, represented by formula (Ar5-6); a divalent group in which two substituted or unsubstituted phenyl groups are bound via a single bond or a divalent group, represented by formula (Ar5-7). In formulae (Ar5-6) and (Ar5-7), $R_5$, $R_6$, $R_7$ and $R_8$ each independently represents a hydrogen atom, an alkyl group having 1 to 4 carbon atoms, an alkoxy group having 1 to 4 carbon atoms, a substituted or unsubstituted phenyl group, a substituted or unsubstituted aralkyl group or a halogen atom.

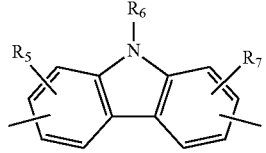
(Ar5-6)

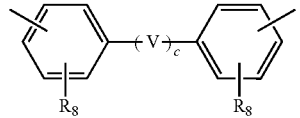
(Ar5-7)

In formula (Ar5-7), c represents 0 or 1, and the case where c is 0 means a single bond. In the case where c is 1, V represents one of groups represented by formulae (V-1) to (V-10). In the following formulae, d represents an integer of from 1 to 10. e represents an integer of from 1 to 3.

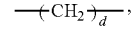
(V-1)

(V-2)

—O—, (V-3)

—S—, (V-4)

(V-5)

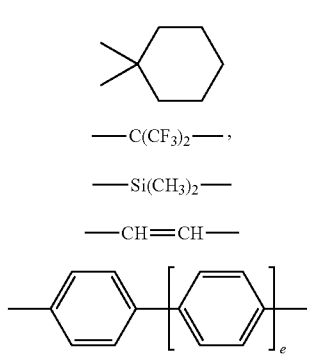

(V-6)

—C(CF$_3$)$_2$—, (V-7)

—Si(CH$_3$)$_2$— (V-8)

—CH═CH— (V-9)

(V-10)

Specific examples of suitable alkyl arylamine ethers thus include, but are not limited to, N,N'-diphenyl-N,N'-bis(3-methoxyphenyl)-[1,1'-biphenyl]-4,4'-diamine, N,N'-diphenyl-N,N'-bis(3-methoxyphenyl)-[1,1':4'1''-terphenyl]-4,4''-diamine, and N,N'-diphenyl-N,N'-bis(3-methoxyphenyl)-naphthyl-2,6-diamine of the following formulae:

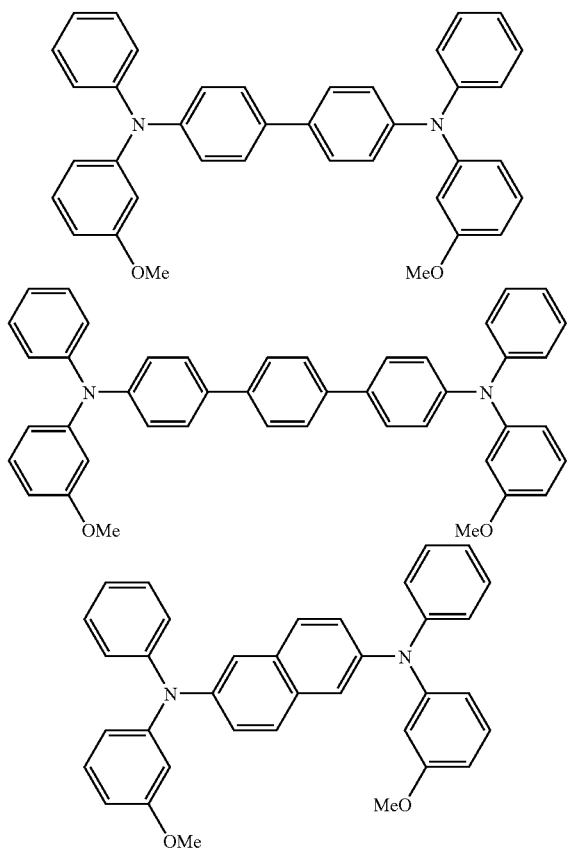

In embodiments, the reagent may be any suitable thiolate precursor attached to any group capable of reducing volatility, and wherein the thiolate is easily removed once the reaction is complete. Suitable thiols comprise, for example, 2-(diethylamine)ethanethiol hydrochloride and polymer supported thiols.

In embodiments, the reagent, 2-(diethylamine)ethanethiolate, may be prepared by mixing its commercially available hydrochloric acid salt, 2-(diethylamine)ethanethiol hydrochloride, with a base in a solvent. Any suitable base capable of neutralizing the hydrochloric acid salt and forming the thiolate in a solvent may be utilized. Suitable bases comprise alkoxide bases, for example, sodium tert-butoxide. Any suitable solvent may be utilized. Suitable solvents comprise dimethylformamide, n-methyl-2-pyrrolidone, tetrahydrofuran, and dimethyl sulfoxide. The alkyl or aryl thiolate can also be generated from a thiol or thiol Brønsted acid salt in situ.

In embodiments, 2-(diethylamine)ethanethiol hydrochloric acid and a solvent are cooled in an ice bath, after which a base, such as sodium tert-butoxide is added to the solution. Other bases that can be used include, for example, sodium methoxide, potassium tert-butoxide, and the like, although generally any commercially available alkali metal or alkali earth metal alkoxide can be used.

In embodiments, the molar equivalents of the components may be, for example, about 1 molar equivalent alkyl arylamine ether, about 1 to about 5 molar equivalents thiol reagent, about 2 to about 10 molar equivalents base, and solvent to form an about 0.05 to about 2 molar solution with respect to alkyl arylamine ether. In specific exemplary embodiments, about 1 molar equivalent alkyl arylamine ether, about 1.25 molar equivalents thiol reagent, about 2.6 molar equivalents base, and solvent to form an about 0.30 molar solution with respect to alkyl arylamine ether.

In embodiments, the alkyl arylamine ether may be added directly to the solution containing the 2-(diethylamine)ethanethiol hydrochloric acid, the base, and the solvent. This solution may be heated at any suitable temperature, such as at reflux temperature. Suitable temperatures may be determined by experimentation and optimization. For example, suitable temperatures may range from about 50° C. or about 75° C. or about 250° C. or about 300° C. such as from about 100° C. to about 200° C. or about 125° C. to about 150° C. In a specific embodiment, for example, reflux occurs at about 140° C. for a solution of n-methyl-2-pyrrolidone, a thiol reagent, sodium tert-butoxide, and an alkyl arylamine ether. The reactants may react for any suitable time to obtain the desired product. For example, suitable reaction times may range from about 30 minutes to about 12 hours. In a specific embodiment, for example, a solution of n-methyl-2-pyrrolidone, a thiol reagent, sodium tert-butoxide, and an alkyl arylamine ether reacted for about 2.5 hours.

In embodiments, a workup may be performed by any conventional methods of isolating the desired product. For example, any acid capable of protonating the phenolate may be used to precipitate the hydroxy arylamine out of solution. Suitable acids include dilute strong acids, such as, 1 molar hydrochloric acid. The solution containing the desired product may be cooled to room temperature after the reaction is completed. Upon addition of a dilute strong acid, the solution may be stirred for about 1 minute to about 60 minutes. In a specific example, a solution was stirred for 30 minutes after the acid was added.

In embodiments, the precipitate may be collected by filtration or any other suitable collection method, such as filtration through a fiber-glass filter.

In embodiments, the collected precipitate may be optionally purified by any suitable or conventional purification technique. Suitable purification techniques comprise dissolving the precipitate in an organic solvent, such as toluene and/or acetone; washing the resulting organic phase with a suitable washing solution, such 1:1 water/brine; drying the organics with a suitable drying agent such as magnesium sulfate; and filtering to form a solid after concentrating the filtrate.

Additional, optional purification methods may be employed to further purify the concentrated solid. Further purification may comprise, for example, suspending the solid in boiling heptane until the distillate is 98° C., cooling the suspension, and filtering the suspension. Further purification may comprise suspending the resulting crude material in refluxing dichloromethane to remove any remaining impurities.

The result is a hydroxyl arylamine, where the protecting (alkyl) group of the arylamine ether has been deprotected to form a hydroxyl arylamine compound.

Examples are set forth herein below and are illustrative of different compositions and conditions that can be utilized in practicing the disclosure. All proportions are by weight unless otherwise indicated. It will be apparent, however, that the disclosure can be practiced with many types of compositions and can have many different uses in accordance with the disclosure above and as pointed out hereinafter.

EXAMPLES

Example 1

In embodiments, a specific example of the method is outlined by the following chemical equation wherein N,N'-diphenyl-N,N'-bis(3-hydroxyphenyl)-[1,1':4'1"-terphenyl]-4,4"-diamine is produced from N,N'-diphenyl-N,N'-bis(3-methoxyphenyl)-[1,1':4"1"-terphenyl]-4,4"-diamine:

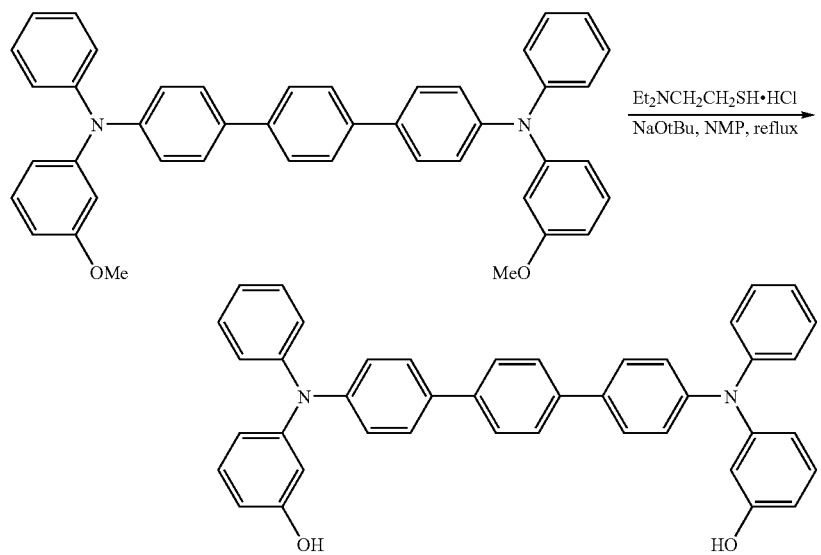

A solution of 2-(diethylamino)-ethanethiol hydrochloride in N-methyl-2-pyrrolidone was cooled in an ice bath and sodium tert-butoxide was added in one portion. The ice bath was removed and N,N'-diphenyl-N,N'-bis(3-methoxyphenyl)-[1,1':4'1"-terphenyl]-4,4"-diamine was added, and the reaction was heated to 140° C. The reaction was monitored by high performance liquid chromatography (HPLC) and was found to be complete within 8 hours. The reaction was cooled to room temperature and methanol (150 mL) was added followed by hydrochloric acid (1 M, aq, 240 mL). Upon addition of hydrochloric acid, a pale yellow precipitate formed. Once all of the acid was added the reaction was stirred at room temperature for 30 minutes. The precipitate was collected by filtration through a fiber-glass filter and dried.

The above reaction resulted in the collection of 126% (90.0 g) of crude pale-yellow powder.

HPLC of the crude material indicated that no starting material or monodeprotected material was present. $^1$H NMR (CDCl$_3$, 300 MHz) revealed no methoxy groups present, but the sample contained N-methyl-2-pyrrolidone (crystallizes with N,N'-diphenyl-N,N'-bis(3-hydroxyphenyl)-[1,1':4'1"-terphenyl]-4,4"-diamine).

The resulting powder was dissolved in toluene (90 g in 200 mL) and once dissolved acetone (300 mL) was added. The organic phase was washed repeatedly with 1:1 water/brine until no N-methyl-2-pyrrolidone remained and the organics were dried with magnesium sulfate, filtered, and concentrated to afford a pale-yellow solid. The material was suspended and heated in refluxing heptane until the distillate was 98° C. The sample was cooled to room temperature and filtered. The crude material (64.8 g) was suspended in refluxing dichloromethane (140 mL) to remove any remaining impurities (found in the filtrate) with the filtercake containing the product as a pale-yellow powder (53.75 g, 75%, >98% pure).

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A method for deprotecting an alkyl arylamine ether to produce a hydroxy arylamine compound, comprising:
    reacting an alkyl amine thiolate or an aryl amine thiolate reagent with an alkyl arylamine ether to yield a hydroxy arylamine compound,
    wherein the alkyl arylamine ether is represented by the following general formula:

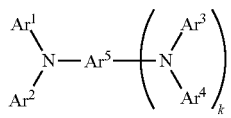

where $Ar^1$, $Ar^2$, $Ar^3$, $Ar^4$ and $Ar^5$ each independently represents a substituted or unsubstituted aryl group, or $Ar^5$ independently represents a substituted or unsubstituted arylene group, and k represents 0 or 1, and at least one of $Ar^1$, $Ar^2$, $Ar^3$ and $Ar^4$ comprises an alkyl aryl ether to be deprotected, and an aromatic ring of the alkyl aryl ether to be deprotected does not have an electron-withdrawing group, wherein the alkyl arylamine ether completely reacts in the presence of from about 1 to about 5 molar equivalents of the thiolate reagent during a reaction time of from about 30 minutes to about 12 hours.

2. The method of claim 1, wherein $Ar^1$, $Ar^2$, $Ar^3$, $Ar^4$, and/or $Ar^5$ may be substituted by one or more groups, the substitutions can be selected from the group consisting of silyl groups, nitro groups, cyano groups, halide atoms, amine groups, hydroxy groups, alkoxy groups, aryloxy groups, alkylthio groups, arylthio groups, aldehyde groups, ketone groups, ester groups, amide groups, carboxylic acid groups, sulfonic acid groups, and mixtures thereof.

3. The method of claim 1, wherein the alkyl or aryl amine thiolate is generated from a thiol or thiol Bronsted acid salt in situ.

4. The method of claim 1, wherein the alkyl or aryl amine thiolate reagent is an alkali metal salt or alkali earth metal salt of 2-(diethylamine)ethanethiol.

5. The method of claim 3, wherein an 2-(diethylamine) ethanethiolate is prepared by a method, comprising mixing 2-(diethylamine)ethanethiol hydrochloric acid with an appropriate base in a solvent.

6. The method of claim 1, wherein the reaction is carried out in a medium comprising a solvent.

7. The method of claim 6, wherein the solvent is selected from the group consisting of dimethylformamide, n-methyl-2-pyrrolidone, tetrahydrofuran, and dimethyl sulfoxide.

8. The method of claim 6, wherein the solvent is dimethylformamide or n-methyl-2-pyrrolidone.

9. The method of claim 5, wherein the base is an alkali metal or alkali earth metal alkoxide.

10. The method of claim 9, wherein the base is sodium tert-butoxide.

11. The method of claim 6, wherein the 2-(diethylamine) ethanethiolate and the alkyl arylamine ether are heated in the solvent above about 80 °C.

12. The method of claim 1, further comprising performing a workup and optional purification of the hydroxy arylamine compound.

13. The method of claim 12, wherein the workup comprises neutralization of the reaction with acid.

14. The method of claim 13, wherein the neutralization is performed by adding a dilute strong Brønsted acid, wherein the acid concentration ranges from about 0.001 to about 10 mol/L.

15. The method of claim 12, wherein the workup is performed by adding about 1 molar hydrochloric acid.

16. The method of claim 1, further comprising, collecting the hydroxy arylamine compound.

17. The method of claim 16, wherein the collecting is performed by filtration through a fiberglass filter.

18. The method of claim 1, further comprising purifying the hydroxy arylamine compound.

19. A method for deprotecting an alkyl arylamine ether to produce a hydroxy arylamine compound, comprising:

reacting an alkyl amine thiolate or an aryl amine thiolate reagent with an alkyl arylamine ether to yield a hydroxy arylamine compound, wherein the alkyl arylamine ether is represented by the following general formula:

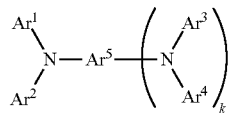

where $Ar^1$, $Ar^2$, $Ar^3$ and $Ar^4$ each independently represents a substituted or unsubstituted aryl group, and $Ar^5$ independently represents a substituted or unsubstituted arylene group, and k represents 1, and at least two of $Ar^1$, $Ar^2$, $Ar^3$ and $Ar^4$ comprise 3-methoxyphenyl to be deprotected, and an aromatic ring of the alkyl arylamine ether to be deprotected does not have an electron-withdrawing group, wherein the alkyl arylamine ether completely reacts in the presence of from about 1 to about 5 molar equivalents of the thiolate reagent during a reaction time of from about 30 minutes to about 12 hours.

20. The method of claim 5, wherein the alkyl arylamine ether is added directly to the solution containing the 2-(diethylamine)ethanethiol hydrochloric acid, the base, and the solvent, wherein base is present in an amount from about 2 to about 10 molar equivalents with respect to the alkyl arylamine ether.

* * * * *